United States Patent [19]

Malamas et al.

[11] Patent Number: 5,480,896
[45] Date of Patent: Jan. 2, 1996

[54] ARALKYL-1,2,4-OXADIAZOLIDINE-3,5-DIONES AS ANTIHYPERGLYCEMIC AGENTS

[75] Inventors: Michael S. Malamas, Jamison, Pa.; Cynthia L. Palka, Bordentown; Iwan Gunawan, Somerset, both of N.J.

[73] Assignee: American Home Products Corporation, Madison, N.J.

[21] Appl. No.: 188,517

[22] Filed: Jan. 27, 1994

[51] Int. Cl.$^6$ .......................... C07D 271/07; A61K 31/41
[52] U.S. Cl. ............................. 514/364; 548/132
[58] Field of Search ............................. 548/132; 514/364

[56] References Cited

U.S. PATENT DOCUMENTS

| 5,002,953 | 3/1991 | Hindley | 514/275 |
| 5,183,825 | 2/1993 | Kees | 514/404 |

FOREIGN PATENT DOCUMENTS

| 9203425 | 3/1992 | WIPO | C07D 263/32 |

OTHER PUBLICATIONS

Goldstein et al., J. Med. Chem. 36, 2238–2240 (1993).

Primary Examiner—Robert Gerstl
Attorney, Agent, or Firm—R. F. Boswell, Jr.

[57] ABSTRACT

This invention relates to novel compounds having antihyperglycemic properties of the formula:

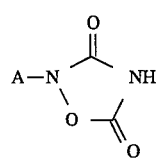

where A is

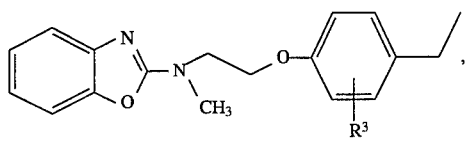

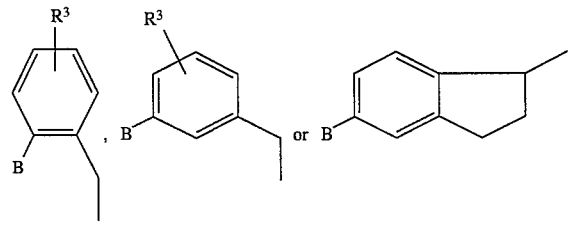

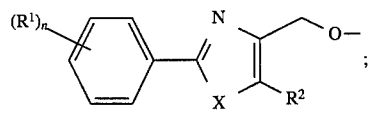

wherein:

n is 1 or 2;

$R^1$ and $R^3$ are independently hydrogen, $C_1$–$C_8$ alkyl, $C_1$–$C_8$ alkoxy, trifluoromethoxy, halogen or trifluoromethyl;

$R^2$ is hydrogen or methyl; and

X is oxygen or sulfur or a pharmaceutically acceptable salt thereof.

2 Claims, No Drawings

ARALKYL-1,2,4-OXADIAZOLIDINE-3,5-DIONES AS ANTIHYPERGLYCEMIC AGENTS

FIELD OF INVENTION

This invention relates to novel aralkyl-1,2,4-oxadiazolidine-3,5-diones as represented by formula I below which have demonstrated antihyperglycemic activity in diabetic (db/db) mice, a genetic animal model of non-insulin dependent diabetes mellitus (NIDDM or Type II). The formula I compounds or pharmaceutical compositions thereof are therefore useful in treating hyperglycemia in mammals having non-insulin dependent diabetes melllitus.

BACKGROUND OF THE INVENTION

Diabetes mellitus is a syndrome characterized by abnormal insulin production, increased urinary output and elevated blood glucose levels. There are two major subclasses of diabetes mellitus. One is the insulin-dependent diabetes mellitus (IDDM or Type I), formerly referred to as juvenile onset diabetes since it was evident early in life, and noninsulin dependent diabetes mellitus (NIDDM or Type II), often referred to as maturity-onset diabetes. Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs requiring much higher doses of insulin than normal. Another shortcoming of insulin is that while it may control hormonal abnormalities, it does not always prevent the occurrence of complications such as neuropathy, retinopathy, glomerulosclerosis, or cardiovascular disorders.

Orally effective antihyperglycemic agents are used to reduce blood glucose levels and to reduce damage to the nervous, retinal, renal or vascular systems through mechanisms affecting glucose metabolism. Such agents act in a variety of different mechanisms including inhibition of fatty acid oxidation, α-glycosidase inhibition, antagonism of α$_2$-receptors and inhibition of gluconeogenesis. Two classes of compounds have predominated: the biguanides as represented by phenformin and the sulfonylureas as represented by tolbutamide (Orinase®). A third class of compounds which has shown antihyperglycemic activity are thiazolidinediones of which ciglitazone is the prototype. Ciglitazone suppresses the symptoms of diabetes - hyperglycemia, hypertriglyceridemia and hyperinsulinemia [Diabetes 32, 804-10 (1983)].

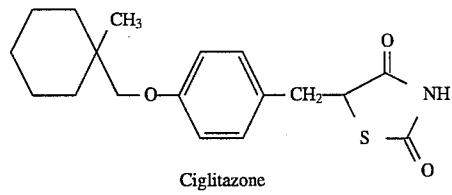

Ciglitazone

Still another class of antihyperglycemic agents are the N-arylalkyl-N-hydroxy ureas and the 2-(arylalkyl)-[1,2,4]oxadiazolidine-3,5-diones. The published PCT patent application WO 92/03425 discloses compounds of the formula:

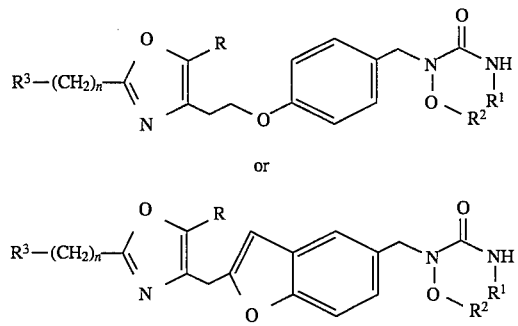

where $R^1$ and $R^2$ are independently H, $C_1$–$C_9$ alkyl, $C_3$–$C_7$ cycloalkyl, phenyl, etc. or $R^1$ and $R^2$ together are carbonyl, which have utility as hypoglycemic or hypocholesteremic agents.

The hypoglycemic properties of these compounds in ob/ob mice are discussed by Goldstein et al. *J. Med. Chem.* 36, 2238–2240 (1993).

SUMMARY

The antihyperglycemic compounds of this invention are represented by formula I:

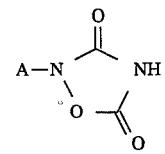

where A is

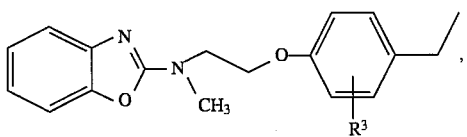

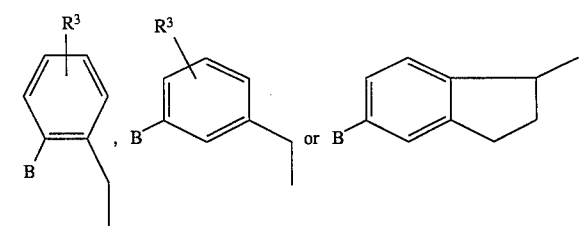

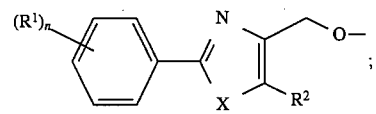

wherein:

n is 1 or 2;

$R^1$ and $R^3$ are independently hydrogen, $C_1$–$C_8$ alkyl, $C_1$–$C_8$ alkoxy, trifluoromethoxy, halogen or trifluoromethyl;

$R^2$ is hydrogen or methyl; and

X is oxygen or sulfur or a pharmaceutically acceptable salt thereof.

To further define the variable terms under $R^1$ and $R^3$, the term $C_1$–$C_8$ alkyl includes straight and branched chain hydrocarbon radicals having from 1 to 8 carbon atoms. The term $C_1$–$C_8$ alkoxy is an —O—$C_1$–$C_8$ alkyl group where $C_1$–$C_8$ alkyl is as defined above. Halogen includes fluoride, chloride, bronfide or iodide radicals.

The term "pharmaceutically acceptable salt" includes hydrates, solvates or cationic addition salts formed between an invention compound and an alkali metal or alkaline earth metal such as sodium, potassium or calcium.

The most preferred compounds of this invention are:

2-[3-(5-methyl-2-phenyl-oxazol-4-ylmethoxy)-benzyl]-[1,2,4]oxadiazolidine-3,5-dione, 2-[3-[5-methyl-2-(4-trifluoromethyl-phenyl)-oxazol-4-ylmethoxy]-benzyl]-[1,2,4] oxadiazolidine-3,5-dione, 2-[3-[5-methyl-2-(3-trifluoromethyl-phenyl)-oxazol-4-ylmethoxy]-benzyl}-[1,2,4] oxadiazolidine-3,5-dione, 2-[3-[2-(3,5-bis-trifluoromethyl-phenyl)-5-methyl-oxazol-4-ylmethoxy]-benzyl][1,2,4 oxadiazolidine-3,5-dione, 2-[3-[5-methyl-2-(4-uifluoromethoxy-phenyl)-oxazol-4-ylmethoxy]-benzyl]-[1,2,4] oxadiazolidine-3,5-dione, 2-[3-fluoro-5-[5-methyl-2-(4-trifluoromethyl-phenyl)-oxazol-4-ylmethoxy]-benzyl] -[1,2,4]oxadiazolidine-3,5-dione, 2-[3-[2-(4-chloro-phenyl)-5-methyl-oxazol-4-ylmethoxy] -benzyl]-[ 1,2,4] oxadiazolidine-3,5-dione, 2-[3-[2-(4-fluoro-phenyl)-5-methyl-oxazol-4- ylmethoxy]-benzyl]-[1,2,4] oxadiazolidine-3,5-dione, 2-[4-methoxy-2[-5-methyl-2-(4-trifluoromethyl-phenyl)oxazol-4-ylmethoxy] -benzyl]-1,2,4]oxadiazolidine-3,5-dione, 2-[3-(2-phenyl-thiazol-4-ylmethoxy)-benzyl]-[ 1,2,4] oxadiazolidine-3,5-dione, -[5-(5-methyl-2-phenyl-oxazol-4-ylmethoxy)-indan-1-yl]-[1,2,4] oxadiazolidine-3,5dione, and 2-[4-[2-(benzoxazol-2-yl)-methyl-amino]-ethoxy]-[1,2, 4 1oxadiazolidine-3,5-dione.

It is one object of this invention to provide novel compounds for treating hyperglycemia due to non-insulin dependent diabetes mellitus. Other objects of this invention are to provide a method of treating hyperglycemia due to non-insulin dependent diabetes mellitus with effective amounts of an invention compound and a pharmaceutical composition therefor.

DETAILED DESCRIPTION OF THE INVENTION

The compounds of the present invention when the group B is present are prepared according to the following Schemes I and II. In scheme I, only meta substitution of the aralkyl group is shown. To prepare the ortho substituted aralkyl compounds, an orthohydroxybenzaldehyde would replace the meta-hydroxybenzaldehyde. The synthesis of invention compounds having an indane moiety is shown in Scheme II.

Scheme I

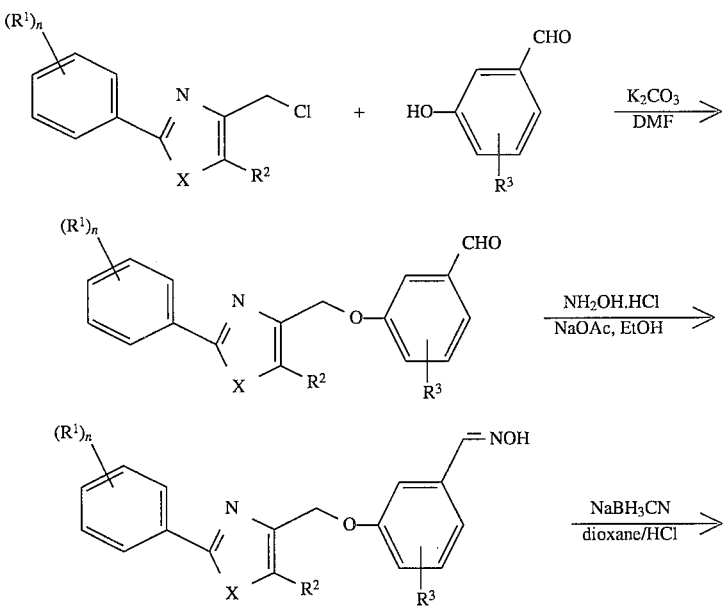

-continued
Scheme I
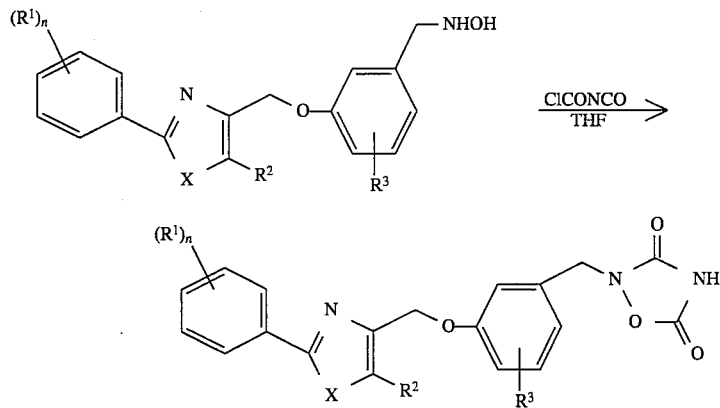
Scheme II
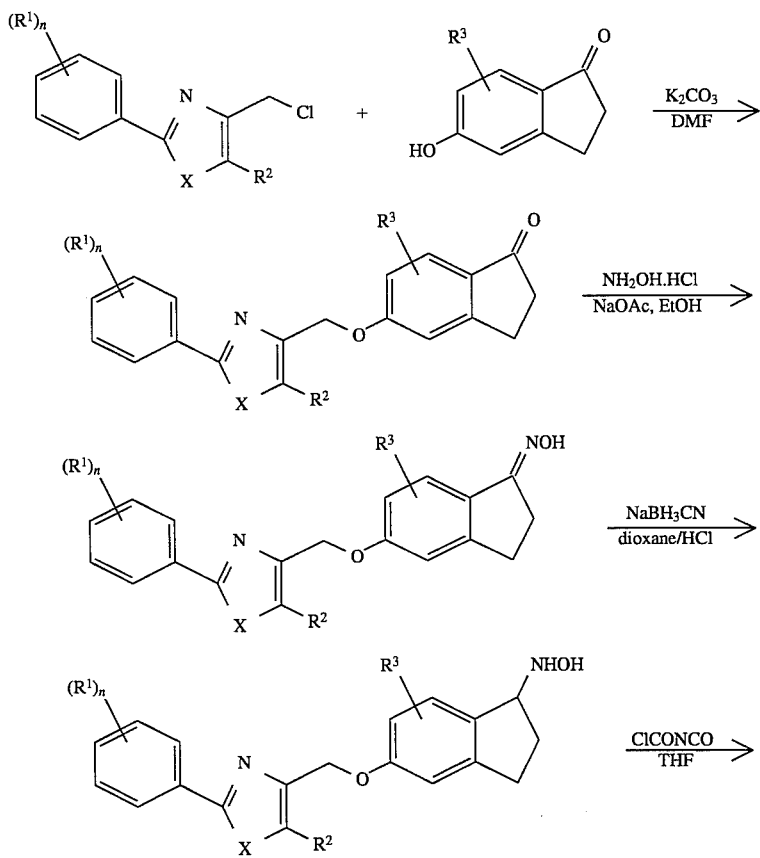

-continued
Scheme II
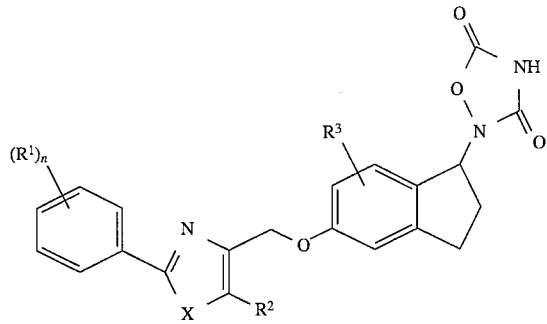
20
The 4-chloromethyl-5-methyl-2-phenyloxazoles are prepared according to Scheme III.
Scheme III
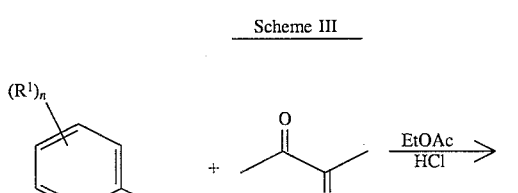
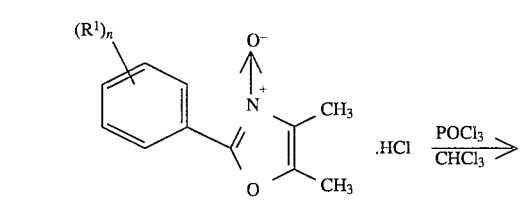
The 4-chloromethyl-2-phenylthiazoles are prepared according to Scheme IV.
Scheme IV
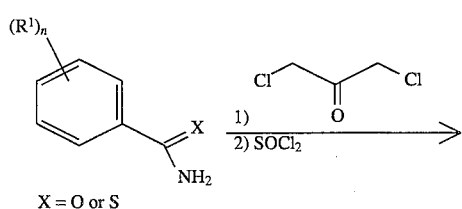
-continued
Scheme IV
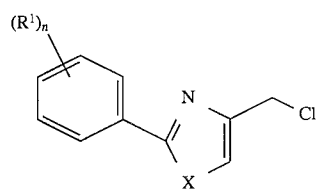
Invention compounds where A is
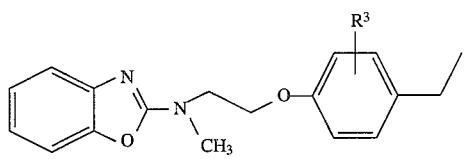
are prepared according to Scheme V.
Scheme V
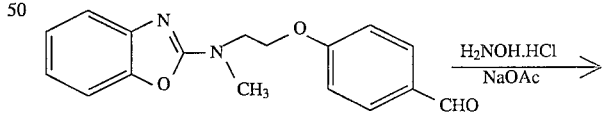
(U.S. Pat. No. 5,002,953)
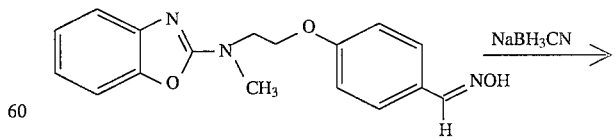
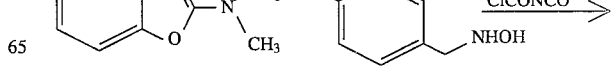

-continued
Scheme V

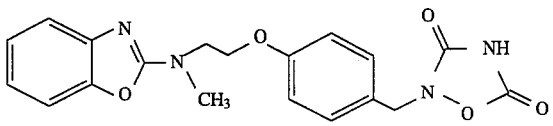

In the above reaction schemes I–V, n, $R^1$, $R^2$, $R^3$, and X are as defined hereinabove.

The following specific examples are included for illustrative purposes only and are not to be construed in any way as limiting the scope of the invention. Those skilled in the art may be aware of still other methods or procedures to prepare invention compounds. All reactants or intermediates are either commercially available or readily prepared according to published procedures. Example 13 is included to show the synthesis of the known compound (PCT published patent application WO 92/03425).

EXAMPLE 1

2-[3-(5-methyl-2-phenyl-oxazol-4-ylmethoxy)-benzyl]-1,2,4]oxadiazolidine-3,5-dione Step a) 3-(5-Methyl-2-phenyl-oxazol-4-ylmethoxy)-benzaldehyde A mixture of 4-chloromethyl-5-methyl-2-phenyl-oxazole (8.25 g, 39.7 mmol), 3-hydroxybenzaldehyde (4.85 g, 39.7 mmol), potassium carbonate (5.49 g, 39.7 mmol) and dimethylformamide (100 mL) was stirred at 80° C. for 8 hours. The mixture was then poured into $H_2O$ and extracted with EtOAc. The organic extracts were dried over $MgSO_4$. Evaporation and purification by flash chromatography on silica gel (eluting solvent EtOAc/hexane 4/1) gave a yellow solid (10.5 g, 90% yield, m.p. 104–105° C.).

Analysis for: $C_{38}H_{36}N_2O_9$

Calc'd: C, 73.71; H, 5.15; N, 4.78

Found: C, 73.88; H, 5.10; N, 4.66

Step b) 3-(5- Methyl- 2-phenyl-oxazol-4-ylmethoxy)-benzaldehyde oxime

In to a solution of 3-(5-methyl-2-phenyl-oxazol-4-ylmethoxy)-benzaldehyde (10.0 g, 34.1 mmol), in ethanol (400 mL) were added hydroxylamine hydrochloride (7.11 g, 102.39 mmol) and a solution of sodium acetate (11.19 g, 136.52 mmol) in $H_2O$(40 mL). The mixture was stirred at room temperature for 10 hours, then poured into $H_2O$, acidified with 2N HCl and extracted with EtOAc. The organic extracts were dried over $MgSO_4$. Evaporation and crystallization from acetone/ether/hexane gave a white solid (8.95 g, 85% yield, m.p. 163–164° C.)

Analysis for: $C_{18}H_{16}N_2O_3$

Calc'd: C, 70.12; H, 5.23; N, 9.09

Found: C, 70.01; H, 5.23; N, 8.90

Step c) N-[3-(5-methyl-2-phenyl-oxazol-4-ylmethoxy)-benzyl]-hydroxylamine

In to a solution of 3-(5-methyl-2-phenyl-oxazol-4-ylmethoxy)-benzaldehyde oxime (8.0 g, 25.9 mmol) in MeOH (400 mL) and THF (80 mL) were added sodium cyanoborohydride (8.06.9 g, 129.5 mmol) and methyl orange (indicator, 20 mg). A solution of 4N HCl in dioxane was then added dropwise in order to maintain a pH range 3 to 4. When a persistent red color was observed the reaction mixture was poured into $H_2O$, basified with 2N NaOH to a pH of about 8 to 9 and extracted with EtOAc. The organic extracts were dried over $MgSO_4$. Evaporation and purification by flash chromatography, on silica gel (eluting solvent EtOAc/MeOH 10/1) gave a white solid (6.5 g, 81% yield, m.p. 123–124° C).

Analysis for: $C_{18}H_{18}N_2O_3$

Calc'd: C, 69.66; H, 5.85; N, 9.03

Found: C, 69.34; H, 5.88; N, 8.75

Step d) 2-[3-(5-methyl-2-phenyl-oxazol-4-ylmethoxy)-benzyl]-[1,2,4] oxadiazolidine-3,5-dione To a cold (–5° C.) solution of N-[3-(5-methyl-2-phenyl-oxazol-4-ylmethyl)-benzyl]hydroxylamine (2.3g, 7.42mmol) in anhydrous THF (30 ml) was added N-(chlorocarbonyl)isocyanate (0.66ml, 8.16mmol) dropwise. The mixture is stirred for 30 minutes, poured into HCl (2N) and extracted with EtOAc. Evaporation and crystallization from acetone/ether gave a white solid (2.22g, 79%), m.p. 148–149° C.

Analysis for: $C_{20}H_{17}N_3O_5$

Calc'd: C, 63.32; H, 4.52; N, 11.08

Found: C, 63.50; H, 4.65; N, 10.82

EXAMPLE 2

2-[3-[5-methyl-2-(4-trifluoromethyl-phenyl)-oxazol-4-ylmethoxyl]-benzyl] [1,2,4]oxadiazolidine-3,5-dione The title compound was prepared in substantially the same manner as described in example 1, and was obtained as a white solid, m.p. 142–143° C.

Analysis for: $C_{21}H_{16}F_3N_3O_5$

Calc'd: C, 56.38; H, 3.60; N, 9.39

Found: C, 56.32; H, 3.60; N, 9.32

EXAMPLE 3

2- [3-[5-methyl-2-(3-trifluoromethyl-phenyl)-oxazol-4-ylmethoxy]-benzyl]-1,2,4] oxadiazolidine-3,5-dione The title compound was prepared in substantially the same manner as described in example 1, and was obtained as a white solid, m.p. 167–168° C.

Analysis for: $C_{21}H_{16}F_3N_3O_5$

Calc'd: C, 56.38; H, 3.60; N, 9.39

Found: C, 56.44; H, 3.54; N, 9.16

EXAMPLE 4

2-[3-[2-(3.5-bis-trifluoromethyl-phenyl)-5-methyl-oxazol-4-ylmethoxylbenzyl] -[1,2,4]-oxadiazolidine-3,5-dione The title compound was prepared in substantially the same manner as described in example 1, and was obtained as a white solid, m.p. 176–178° C.

Analysis for: $C_{22}H_{15}F_6N_3O_5$

Calc'd: C, 51.27; H, 2.93; N, 8.15

Found: C, 51.23; H, 2.84; N, 8.09

Example 5

2-[ 3-[5-methyl- 2-( 4-trifluoromethoxy-phenyl)-oxazol-4- ylmethoxy] -benzyl]-1,2,4]-oxadiazolidine-3,5-dione The title compound was prepared in substantially the same manner as described in example 1, and was obtained as a white solid, m.p. 162–163° C.

Analysis for: $C_{21}H_{16}F_3N_3O_6$

Calc'd: C, 54.43; H, 3.48; N, 9.07

Found: C, 54.51; H, 3.35; N, 8.97

EXAMPLE 6

2-[3-fluoro-5-[5-methyl-2-(4-trifluoromethyl-phenyl)-oxazol-4-ylmethoxylbenzy]-benzyl]-[1,2,4]oxadiazolidine-3,5-dione The title compound was prepared in substantially the same manner as described in example 1, and was obtained as a white solid, m.p. 159–161 ° C.

Analysis for: $C_{21}H_{15}F_4N_3O_5$

Calc'd: C, 54.20; H, 3.25; N, 9.03

Found: C, 54.28; H, 3.06; N, 8.94

EXAMPLE 7

2-[3-[2-(4-chloro-phenyl)-5-methyl-oxazol-4-ylmethoxy]-benzyl]-1,2,4] oxadiazolidine-3,5-dione The title compound was prepared in substantially the same manner as described in example 1, and was obtained as a white solid, m.p. 166–167° C.

Analysis for: $C_{20}H_{16}ClN_3O_5$

Calc'd: C, 58.05; H, 3.90; N, 10.15

Found: C, 58.38; H, 3.74; N, 10.34

EXAMPLE 8

2-[3-[2-(4-fluoro-phenyl)-5-methyl-oxazol-4-ylmethoxyl]-benzyl]-[1,2,4] oxadiazolidine-3,5-dione The title compound was prepared in substantially the same manner as described in example 1, and was obtained as a white solid, m.p. 163–164° C.

Analysis for: $C20H16FN3O_5$

Calc'd: C, 60.45; H, 4.06; N, 10.58

Found: C, 60.70; H, 3.97; N, 10.69

2- [4- methoxyl-2-[5-methyl-2-(4-trifluoromethyl-phenyl)-oxazol-4 -ylmethoxyl-benzyl]-[1,2,4]oxadiazolidine-3,5-dione The title compound was prepared in substantially the same manner as described in example 1.

2-Hydroxy-4-methoxybenzaldehyde was used in place of 3-hydroxybenzaldehyde. The title compound was obtained as a white solid, m.p. 168–170° C.

Analysis for: $C_{22}H_{18}F_3N_3O_6$

Calc'd: C, 55.35; H, 3.80; N, 8.80

Found: C, 55.50; H, 3.73; N, 8.51

EXAMPLE 10

2-[3-(2-phenyl-thiazol-4-ylmethoxy)-benzyl]-[1,2,4]oxadiazolidine-3,5-dione

The title compound was prepared in substantially the same manner as described in example 1, and was obtained as a white solid, m.p. 139–140° C.

Analysis for: $C_{19}H_{15}N_3O_4S$

Calc'd: C, 59.83; H, 3.96; N, 11.02

Found: C, 59.92; H, 3.85; N, 10.81

EXAMPLE 11

2-[5-(5-methyl-2-phenyl-oxazol-4-ylmethoxy)-indan-1-yl]-[1,2,4] 1,2,4]oxadiazolidine-3,5-dione The title compound was prepared in substantially the same manner as described in example 1.

4-Hydroxy-1-indanone was used in place of 3-hydroxybenzaldehyde. The title compound was obtained as a white solid, m.p. 162–163° C.

Analysis for: $C_{22}H_{19}N_3O_5$

Calc'd: C, 65.18; H, 4.72; N, 10.37

Found: C, 65.36; H, 4.69; N, 10.03

EXAMPLE 12

2-[4-[2-(benzoxazol-2-yl)-methyl-aminol-ethoxyl-[1,2,4]oxadiazolidine-3,5-dione

The title compound was prepared in substantially the same manner as described in example 1, using 4-[2-[N-Methyl-N-(2-benzoxazolyl)amino]ethoxy]benzaldehyde (prepared according to U.S Pat. 5,002,953, 1991) in place of 3-hydroxybenzaldehyde. The title compound was obtained as a white solid, m.p. 155–157° C.

Analysis for: $C_{19}H_{18}N_4O_5$

Calc'd: C, 59.68; H, 4.75; N, 14.65

Found: C, 59.36; H, 4.75; N, 14.46

EXAMPLE 13

2- [ 4-( 5-methyl-2-phenyl-oxazol-4- ylethoxy)-benzyl]-[1,2,4] oxadiazolidine-3,5-dione The title compound was prepared as a reference to the prior art, according to the published PCT patent application WO 92-03425.

Analysis for: $C_{21}H_{19}N_3O_5$

Calc'd: C, 64.12; H, 4.87; N, 10.68

Found: C, 64.37; H, 4.89; N, 10.57

PHARMACOLOGY

The diabetic db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia (1). Furthermore, the db/db mouse will eventually develop some of the long-term complications that have been associated with diabetes mellitus (1). In spite of these commonalities, the acute administration of sulfonylureas (even at extremely high doses) will not reduce the hyperglycemia of the db/db mouse (2). The ability of a few other hypoglycemic agents to be effective in this species suggest that the other agents have mechanism of action which are different from that of the sulfonylureas (2,3,4,5). Such compounds, therefore, are more likely to be efficacious in the population of type II diabetic patients that do not respond to sulfonylurea therapy.

Determination of Blood Glucose Lowering in db/db Mice.

On the morning of Day 1, 35 mice [male diabetic db/db (C57BL/KsJ) mice (Jackson Laboratories), 2–7 months of age and 50–70 g] were fasted for 4 hours, weighed and a baseline blood sample (15–30 gl) was collected from the tail-tip of each mouse without anesthesia, and placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels (N=6 for vehicle and N=4 for each drug group). On the afternoon of Days 1, 2 and 3, the vehicle, control or test drugs were administered (p.o.) to the ad libitum fed mice. On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hrs after drug administration. The plasma was separated and levels of glucose in plasma was determined by the Abbott VP Analyzer.

For each mouse, the percent change of its plasma glucose level on Day 4 (mean of the 2 and 4 hr samples) from respective level before drug administration (Day 1 baseline sample) is determined as follows:

mean of 2 and 4 hr samples (Day4) × 100

Baseline Sample (Day 1)

Analysis of variance followed by Dunnett's multiple comparison (one-sided) will be used to estimate the degree of statistical significance of the difference between the vehicle control group and the individual drug-treated groups. A drug will be considered active, at the specific dosage administered, if the difference of the plasma glucose level has a $p<0.05$. The actual difference between the mean percent change of the vehicle and drug-treated groups is shown in Table 1.

The positive control, ciglitazone produces a 18 to 34% decrease in plasma glucose levels at 100 mg/kg/day×4 days, p.o.

The compound of Example 13 is the most active compound reported by Goldstein et al., J. Med Chem. 36, 2238–2240 (1993), and is included in the results shown in Table I for comparison. The invention compounds of Examples 1–12 are comparable or better (Examples 2 and 5) than the known compound of example 13.

TABLE 1

| Compound of Example No. | Dose mg/kg. p.o. | % Change glucose |
|---|---|---|
| 1 | 100 | −47 |
| 2 | 100 | −60 |
| 2 | 20 | −37 |
| 3 | 100 | −60 |
| 4 | 100 | −54 |
| 5 | 100 | −64 |
| 5 | 20 | −46 |
| 6 | 100 | −51 |
| 7 | 100 | −37 |
| 8 | 100 | −36 |
| 9 | 100 | −42 |
| 10 | 100 | −27 |
| 11 | 100 | −26 |
| 12 | 100 | −34 |
| 13 | 100 | −39* |
| ciglitazone (Positive control) | 100 | −18 TO −34 |

*average of two assays

References:

1. Coleman, D. L. (1982) Diabetes-obesity syndromes in mice. Diabetes 31 (Suppl. 1); 1–6.

2. Tutwiler, G. F., T. Kirsch, and G. Bridi (1978). A pharmacologic profile of McN495 [N-( 1-methyl-2-pyrrolidinylidene )-N'-phenyl- 1-pyrrolidine-carboximidamide], a new, orally effective hypoglycemic agent. Diabetes 27:856–857.

3. Lee, S.M., G. Tutwiler, R. Bressler, and C. H. Kircher (1982). Metabolic control and prevention of nephropathy by 2-tetradecylglycidate in the diabetic mouse (db/db). Diabetes 31: 12–18.

Chang, A. Y., B. W. Wyse, B. J. Gilchrist, T. Peterson, and R. Diani (1983) Ciglitazone, a new hypoglycemic agent. 1. Studies in ob/ob and db/db mice, diabetic Chinese hamsters, and normal and streptozocin-diabetic rats. Diabetes 32: 830–838.

5. Hosokawa, T., K. Ando, and G. Tamura (1985). An ascochlorin derivative, AS-6, reduces insulin resistance in the genetically obese diabetic mouse, db/db. Diabetes 34: 267–274.

Pharmaceutical Composition

Based on the results of the pharmacological assay, the compounds of this invention are useful in the treatment of hyperglycemia in diabetes mellitus.

The compounds may be administered neat or with a pharmaceutical carrier to a mammal in need thereof. The pharmaceutical carrier may be solid or liquid and the active compound shall be a therapeutically effective amount.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intrapefitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. A dosage range of from 0.1 to 200 mg/kg/day is contemplated, with a preferred dosage of from 0.1 to 100 mg/kg/day. Due to uncertainty in relating laboratory mouse study data to other mammals, the degree of hyperglycemia, and the compound selected, the dosages used in the treatment of non-insulin dependent diabetes mellitus must be subjectively determined by a physician or veterinarian according to standard medical or veterinary practice.

What is claimed is:

1. A compound according to the formula:

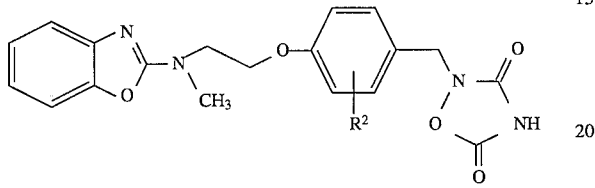

wherein $R^2$ is hydrogen or methyl; or a pharmaceutically acceptable salt thereof.

2. A method of treating elevated blood glucose in a mammal having elevated blood glucose which comprises administration thereto of all effective amount of a compound of the formula:

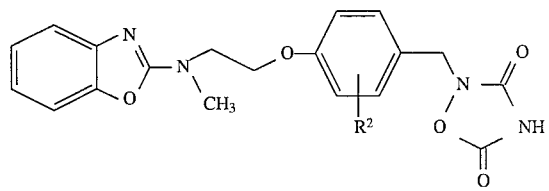

wherein $R^2$ is hydrogen or methyl; or a pharmaceutically acceptable salt thereof.

* * * * *